United States Patent [19]

Vanlautem et al.

[11] 4,365,088
[45] Dec. 21, 1982

[54] PROCESS FOR THE MANUFACTURE OF β-HYDROXYBUTYRIC ACID AND ITS OLIGOCONDENSATES

[75] Inventors: Noël Vanlautem, Wavre; Jacques Gilain, Brussels, both of Belgium

[73] Assignee: Solvay & Cie, Brussels, Belgium

[21] Appl. No.: 280,082

[22] Filed: Jul. 2, 1981

[30] Foreign Application Priority Data

Jul. 3, 1980 [FR] France .................. 80 14889

[51] Int. Cl.$^3$ .............................. C07C 59/00
[52] U.S. Cl. .................... 562/579; 560/185
[58] Field of Search .......... 562/579; 560/185

[56] References Cited

U.S. PATENT DOCUMENTS

| | | | |
|---|---|---|---|
| 2,847,465 | 8/1958 | Robertson | 562/579 |
| 3,202,702 | 8/1965 | Olivier | 562/579 |
| 3,407,129 | 10/1968 | Petrocelli et al. | 562/579 |
| 4,229,354 | 10/1980 | Bogdanovic | 562/579 |

*Primary Examiner*—Paul J. Killos
*Attorney, Agent, or Firm*—Spencer & Kaye

[57] ABSTRACT

Poly-β-hydroxybutyrates obtained by biosynthesis are hydrolyzed in a reaction mixture containing poly-β-hydroxybutyrates, water and an acid catalyst, in a solvent.

10 Claims, No Drawings

PROCESS FOR THE MANUFACTURE OF β-HYDROXYBUTYRIC ACID AND ITS OLIGOCONDENSATES

BACKGROUND OF THE INVENTION

The present invention relates to a process for the manufacture of β-hydroxybutyric acid and its oligocondensates from its polycondensates obtained by biosynthesis.

Numerous microorganisms are capable of synthesising polycondensates of β-hydroxybutyric acid (poly-β-hydroxybutyrates), and various techniques, such as extraction, are known for separating the poly-β-hydroxybutyrates from the biomasses.

As β-hydroxybutyric acid is a very valuable intermediate for the fine chemicals industry, various attempts have been made to synthesise it starting from its polycondensates obtained by biosynthesis. However, all the processes envisaged hitherto for this purpose exhibit the serious disadvantage of leading not to the acid itself but to its derivatives. These known processes therefore necessitate the subsequent conversion of these derivatives to the acid, which makes them too complicated and too expensive to be suitable for industrial use.

Thus, a first of these known methods consists in saponifying the poly-β-hydroxybutyrates by means of an alkaline solution, so as to form alkali metal salts of β-hydroxybutyric acid. This method possesses the additional disadvantage of resulting in the formation of large amounts of undesired by-products such as the salt of crotonic acid. A second method which has already been proposed consists in treating the poly-β-hydroxybutyrates with anhydrous hydrazine, which makes it possible to obtain crystals of the hydrazide of D(—)-β-hydroxybutyric acid, and this can only be converted to the acid using stoichiometric amounts of acids such as sulphuric acid or hydrochloric acid, the yields observed being furthermore very low. In accordance with a third known method, methanolysis is carried out and this gives oligocondensates in the form of methyl esters and also the methyl ester of the acid.

SUMMARY OF THE INVENTION

The object of the present invention is to provide a process which leads directly to β-hydroxybutyric acid or its oligocondensates.

For this purpose, the present invention provides a process for the manufacture of β-hydroxybutyric acid or its oligocondensates from its polycondensates, in accordance with which the polycondensates are subjected to hydrolysis in a liquid reaction mixture containing a solvent, polycondensates, an acid catalyst and water.

DETAILED DESCRIPTION OF THE INVENTION

The poly-β-hydroxybutyrates, also referred to as poly-β-hydroxybutyric acids, which are used according to the invention can be crude products or pure products obtained from a biomass by any known means of separation. The origin of the biomass is not significant for the process according to the invention. The biomass can thus originate from various microorganisms and especially from bacteria, as has been described in Angewandte Chemie, 1962, 74th year, No. 10, pages 342 to 346, by Schlegel and Gottschalk.

Preferably, the starting materials used are poly-β-hydroxybutyrates separated from the biomass by extraction with solvents which can be used in the process according to the invention and which are described below. This makes it possible to carry out the process according to the invention directly after the extraction, in the same solvent, without discontinuity between the operations.

The poly-β-hydroxybutyrates used generally have a weight-average molecular weight ($\overline{M}_w$) of more than 100,000. Usually, this molecular weight is between 500,000 and 3,000,000 and most frequently between 700,000 and 1,500,000. It can vary according to the origin of the poly-β-hydroxybutyrate used.

In the process according to the invention, the reaction mixture can consist of one phase or several different phases. However, the process is preferably carried out with a reaction mixture in which the solvent, the poly-β-hydroxybutyrates and the water constitute only one homogeneous liquid phase. If the acid catalyst is liquid, it is preferably chosen so as to be in the totally dissolved form in this liquid phase. Thus, the process is preferably carried out in the absence of a second liquid phase or of a solid phase containing undissolved poly-β-hydroxybutyrates.

The solvents used according to the invention can be chosen from amongst all the organic solvents which are capable of solubilising the poly-β-hydroxybutyrates, whilst at the same time being chemically inert with respect to the latter, to the water and to the acid catalyst used. The solvents can consist of a single compound, which is pure or of technical grade, or of a mixture of several compounds.

Preferably, the solvents are chosen from amongst those which can be used for the extraction of the poly-β-hydroxybutyrates from the biomasses, and in particular from amongst substituted or, preferably, unsubstituted halogenated solvents. Amongst the latter, the chloroethanes and chloropropanes described in French Pat. No. 79/01,862, filed on Jan. 22, 1979 in the name of SOLVAY & Cie, and also methylene chloride and chloroform, are suitable. Good results have been obtained with methylene chloride, chloroform, 1,2-dichloroethane, 1,1,2-trichloroethane, 1,1,2,2-tetrachloroethane and 1,2,3-trichloropropane. The best results have been obtained with chloroform and very particularly with 1,2-dichloroethane.

The amounts of solvent to be used, relative to the amounts of poly-β-hydroxybutyrates, can vary within wide limits and are not critical. However, since the hydrolysis rate is a function of the polymer concentration, the process is preferably carried out with the highest possible concentrations.

As the poly-β-hydroxybutyrates are the more soluble in the solvents, the lower their molecular weight, it is advantageous to concentrate the reaction mixture progressively as the hydrolysis proceeds. To do this, the solvent can advantageously be distilled progressively, so that the reaction mixture becomes increasingly concentrated.

The acid catalysts which are used according to the invention can be chosen from amongst all the Brönsted and Lewis acids. It is usually preferred to use Brönsted acids having a $pK_A$ of less than 4 and more preferably of less than 2.5. Amongst these BrEML/o/ nsted acids, it is preferred to employ sulphuric acid, hydrochloric acid and phosphoric acid and their derivatives, and also sulphonic acids. Sulphonated resins are also suitable.

The catalysts which have given the best results are alkyl-, aryl-, alkylaryl- and aryl-alkyl-sulphonic acids and also sulphuric acid. Sulphuric acid and para-toluenesulphonic acid are very particularly preferred.

The amount of acid catalyst to be used in the reaction mixture is not in itself critical. The catalyst concentrations, relative to the monomeric units present in the poly-$\beta$-hydroxybutyrates used, can reach values of 100 mol %. However, this ratio is usually between 0.1 and 40 % and preferably between 0.5 and 10%.

The water can be introduced into the reaction medium at any time before or 10%.

The water can be introduced into the reaction medium at any time before or during the hydrolysis. Thus, the process according to the invention makes it possible to use crude poly-$\beta$-hydroxybutyrates which are not in the anhydrous from, and with non-anhydrous solvents and catalysts of technical grade.

The amount of water to be used in the reaction mixture is preferably chosen so that the liquid reaction medium is not heterogeneous, at any time, as a result of the appearance of two different liquid phases, namely an organic phase and an aqueous phase. Consequently, in this case, the amount of water used is chosen as a function of the nature of the solvent, the temperature, the pressure and the molecular weight of the poly-$\beta$-hydroxybutyrate at the time in question. As the water is generally poorly miscible with the solvents preferably used according to the invention, it is therefore advantageously added in several stages or continuously throughout the hydrolysis, taking care not to exceed the solubility limit of the water in the reaction medium.

Furthermore, it has been found that the solubility of the water in the reaction medium increases progressively as the hydrolysis proceeds, and that the molecular weight of the poly-$\beta$-hydroxybutyrates decreases. Moreover, when the hydrolysis has proceeded so that the degree of polymerisation has reached a value ranging from about 2 to 10, and so that oligocondensates are therefore present, the solubility of the latter in the water is sufficient for it to be possible to continue the hydrolysis in an aqueous liquid phase. To do this, it is possible to remove the solvent by simple distillation and, if appropriate, to add water. It is thus possible to continue the hydrolysis in a homogeneous aqueous liquid phase and to obtain the $\beta$-hydroxybutyric acid with high yields, without the formation of large amounts of by-products.

Apart from the solvent, the poly-$\beta$-hydroxybutyrates, the water and the acid catalyst, the reaction mixture, can contain various other constituents. Amongst the latter, there may be mentioned bleaching agents such as peroxide compounds of the hydrogen peroxide type, which make it possible to obtain depolymerised products of enhanced whiteness. This proves to be particularly advantageous if the process is carried out starting from poly-$\beta$-hydroxybutyrates which have not been purified beforehand. The concentration of these bleaching agents must be adjusted so as not to cause chemical degradation of the products.

The process according to the invention can be carried out at low temperature, but is usually carried out at temperatures above 25° C. In general, for reasons of convenience, it is not carried out at temperatures above 150° C. Preferably, the process is carried out at temperatures between 50° and 125° C. Furthermore, it is particularly advantageous to carry it out at the reflux temperature of the medium, at the pressure in question, so as to be able to remove the solvent progressively by distillation, as has been explained above.

The pressure applied during the process is not in itself critical and is generally below 10 bars. Preferably, the process is carried out at pressures of between 0.05 and 5 bars. Very particularly, it is preferably carried out at atmospheric pressure.

As regards the duration of the hydrolysis, it is self-evident that this is chosen as a function of the product which it is desired to obtain. More particularly, in the case where it is desired to obtain oligocondensates, this duration can be determined, in each individual case, as a function of the degree of polymerisation of the oligocondensates which it is desired to obtain. Thus, the process according to the invention makes it possible easily to obtain oligocondensates having a weight-average molecular weight of less than 50,000 and more particularly of less than 10,000.

The process according to the invention can be carried out continuously or batchwise in any installation which makes it possible to combine the operating conditions described above.

The $\beta$-hydroxybutyric acid or the oligocondensates obtained by the process according to the invention can be separated from the reaction medium by any known means. Usually, this operation is carried out by means of one or more distillations and filtrations, which may or may not be followed by washing with water or organic solvents.

The $\beta$-hydroxybutyric acid oligocondensates can be used for their hydroxyl or carboxyl groups and especially as an energy reserve in animal feeds.

The following examples serve to illustrate the invention.

EXAMPLE 1 (comparison)

4.3 g of a poly-$\beta$-hydroxybutyrate having a weight-average molecular weight ($\overline{M}_w$) of 963,000, dispersed in 100 cm$^3$ of demineralised water, are introduced into a 250 cm$^3$ round-bottomed flask equipped with a stirrer, athermometer, a dropping funnel and a water-cooled condenser. 2.9 cm$^3$ of 35 N sulphuric acid are added to the medium and the mixture is heated at the boil for 6 hours with mechanical stirring. The reaction medium is collected by filtration on a G4 filter and washed copiously with demineralised water. After drying to constant weight under 2.5 kPa at 50° C., 4.22 g of a poly-$\beta$-hydroxybutyrate having an average molecular weight $M_w$ of 233,000 are recovered.

EXAMPLE 2

4.3 g of a poly-$\beta$-hydroxybutyrate having a weight-average molecular weight ($\overline{M}_w$) of $1.3 \cdot 10^6$ are introduced into a 500 cm$^3$ round-bottomed flask fitted with a stirrer, a thermometer, a dropping funnel and a water-cooled condenser, and are dissolved in 250 cm$^3$ of 1,2-dichloroethane by heating the solvent under reflux. After total dissolution of the polymer, 0.43 g of para-toluenesulphonic acid monohydrate and 4.5 g of water are added. The mixture, which has become heterogeneous as the result of the appearance of two liquid phases, is heated under reflux for a further 6 hours and 5 cm$^3$ samples of reaction mixture are taken during this operation. In each case, this gives a poly-$\beta$-hydroxybutyrate having the molecular weight indicated in Table I below.

TABLE I

| Sample | Number-average molecular weight ($\overline{M}_n$) | Weight-average molecular weight ($\overline{M}_w$) |
| --- | --- | --- |
| after 2 hours | 7,800 | 16,000 |
| after 3 hours | 4,300 | 10,000 |
| after 4 hours | 4,300 | 10,000 |
| after 5 hours | 4,300 | 10,000 |

EXAMPLE 3

The procedure of Example 2 is followed, but instead of being carried out in a heterogeneous medium, the process is carried out in a homogeneous medium, that is to say that the medium used contains only 0.81 g of water, which, at the boiling point (about 80° C.), constitutes an amount which is perfectly miscible with the 1,2-dichloroethane. The results observed are summarised in Table II below.

TABLE II

| Sample | Number-average molecular weight ($\overline{M}_n$) | Weight-average molecular weight ($\overline{M}_w$) |
| --- | --- | --- |
| after 2 hours | 1,890 | 4,000 |
| after 3 hours | 1,320 | 2,800 |
| after 4 hours | 1,140 | 2,300 |
| after 5 hours | 970 | 2,000 |

A comparison of Examples 1, 2 and 3 shows that the hydrolysis of the poly-$\beta$-hydroxybutyrates in a heterogeneous aqueous medium (Example 1) is insignificant. A comparison of Examples 2 and 3 shows that this hydrolysis in a heterogeneous mixed organic solvent-/water medium (Example 2) is more effective, but nevertheless slower than the hydrolysis carried out in a homogeneous organic solvent medium (Example 3). Furthermore, it makes it possible to achieve the lowest molecular weights.

EXAMPLE 4

125 cm$^3$ of a solution containing 40 g/liter of poly-$\beta$-hydroxybutyrate in 1,2-dichloroethane, originating from extraction, are introduced into the reactor of Example 1. The weight-average molecular weight ($\overline{M}_w$) is 1.33.10$^6$. 1.06 cm$^3$ of 35 N H$_2$SO$_4$ are added thereto. This mixture is heated to the boil at atmospheric pressure. The solution is concentrated by distillation of the solvent and continuous addition of 635 cm$^3$ of the extraction solution, so as to keep the reaction volume at 125 cm$^3$. After 3 hours 30 minutes, a poly-$\beta$-hydroxybutyrate having a number-average molecular weight ($\overline{M}_n$) of 4,000 is obtained in a concentration of 2.83 mols/liter.

The water-cooled condenser is then placed vertically on the round-bottomed flask so that the solution can be heated under reflux without removing solvent. 3.2 g of water are then added, in less than 1 minute, to the solution heated to the reflux temperature. A further 1.6 g of water are added after 4.0 hours and a further 1.6 g of water are added after 7.7 hours at the boil. After 9 hours, oligocondensates having a number-average molecular weight ($\overline{M}_n$) of 650 were obtained after purification and drying to constant weight. These products are brownish in colour.

EXAMPLE 5

The process is carried out under the same conditions as in Example 4, but instead of adding water, the same amounts of a 30 % strength solution of hydrogen peroxide in water are added.

The number-average molecular weight ($\overline{M}_n$) of the oligocondensates obtained is essentially the same as that obtained in Example 4, but the oligomers are now in the form of a white powder.

Examples 4 and 5 show that it is possible to carry out the hydrolysis of crude poly-$\beta$-hydroxybutyrates, originating directly from the biomass, with the aid of acid catalysis, in a homogeneous organic solvent/ water medium, by means of a solution which has been concentrated and partially depolymerised (Examples 4 and 5), and that it is possible to obtain perfectly white oligomers using an aqueous solution of a peroxide solution (Example 5).

EXAMPLE 6

A solution, in 1,2 dichloroethane, containing 40 g/liter of a poly-$\beta$-hydroxybutyrate having a weight-average molecular weight ($\overline{M}_w$) of 1.33.10$^6$, and also 7.0 g of p-toluenesulphonic acid, are introduced gradually into a 500 cm$^3$ round-bottomed flask fitted with a mechanical stirrer, a thermometer, a dropping funnel and a water-cooled condenser making it possible to distill the liquid phase, and the solvent is distilled continuously so as to obtain, after 4 hours, 250 cm$^3$ of a concentrated solution containing 256 g/liter of poly-$\beta$-hydroxybutyrate having a number-average molecular weight ($\overline{M}_n$) of 9,200.

This solution is then heated under reflux in the same apparatus modified so that the water-cooled condenser is fitted vertically and can function as a reflux column. When the solution reaches the reflux temperature, 6.7 cm$^3$ of water are added all at once, and after an operating time of 4 hours, an additional 3.4 cm$^3$ of water are added. The reaction is stopped after 6.5 hours and the oligocondensates obtained have a number-average molecular weight ($\overline{M}_n$) of 270.

The equipment is then modified again so that, as at the start, it can function as a distillation apparatus, and the 1,2-dichloroethane is continuously removed by distillation in the course of 2.5 hours, whilst water is added gradually with the aid of the dropping funnel. The aqueous solution is heated for a further 4 hours under reflux and this finally gives $\beta$-hydroxybutyric acid, which is isolated by distillation under a reduced pressure of less than 15 Pa, after neutralisation of the p-toluenesulphonic acid with 2 N NaOH. The molar yield of distilled acid, relative to the starting polymer, is 62%. The formation of crotonic acid was never observed during the various reaction steps.

We claim:

1. Process for the manufacture of $\beta$-hydroxybutyric acid or its oligocondensates from its polycondensates, comprising subjecting the polycondensates to hydrolysis in a liquid reaction mixture containing a solvent, the polycondensates, an acid catalyst and water.

2. Process according to claim 1, wherein the solvents, the polycondensates and the water are kept in the form of a homogeneous liquid phase.

3. Process according to claim 2, wherein the homogeneous phase is an organic phase.

4. Process according to any one of claims 1 to 3, wherein the solvent is a halogenated solvent.

5. Process according to claim 4, wherein the solvent is at least one compound chosen from amongst chloropropanes, chloroethanes, methylene chloride and chloroform.

6. Process according to any one of claims 1 to 3, wherein the acid catalyst used is chosen from amongst sulphuric acid and alkyl-, aryl-, alkylaryl- or arylalkyl-sulphonic acid.

7. Process according to any one of claims 1 to 3, wherein the reaction mixture is concentrated progressively during the hydrolysis, by distillation of the solvent.

8. Process according to any one of claims 1 to 3, wherein the solvent is removed when water-soluble oligocondensates have been obtained, and the hydrolysis is continued in the aqueous liquid phase.

9. Process according to any one of claims 1 to 3, wherein the reaction mixture is kept at a temperature between 50° and 125° C.

10. Process according to any one of claims 1 to 3, wherein a peroxide compound is added to the reaction mixture.

* * * * *